United States Patent [19]
Hall et al.

[11] Patent Number: 5,223,253
[45] Date of Patent: Jun. 29, 1993

[54] BOVINE VACCINE COMPOSITIONS AND METHOD FOR PREVENTING TRICHOMONAS INFECTIONS USING SAME

[75] Inventors: Mark Hall, Reno, Nev.; Bonnie Wallace, Fort Dodge, Iowa; William M. Acree, Fort Dodge, Iowa; Lloyd G. Chavez, Fort Dodge, Iowa

[73] Assignee: American Home Products Corporation, New York, N.Y.

[21] Appl. No.: 411,921

[22] Filed: Sep. 28, 1989

[51] Int. Cl.$^5$ ................ A61K 39/00; A01N 63/00
[52] U.S. Cl. .................................... 424/88; 424/92; 424/450; 530/350; 435/252.1
[58] Field of Search ............ 424/88, 93, 92, 450; 530/350; 435/252.1

[56] References Cited

PUBLICATIONS

Bondurant et al., *California Cattleman*, pp. 10–11, Feb. 1988.
Burgess, *Experimental Parasitology*, , vol. 62, pp. 266–274, 1986.
Hall et al., Am. J. Vet. Res., vol. 47, No. 12, pp. 2549–2553, 1986.
Morgan, Aur. J. Vet. Res. vol. 54, pp. 54–56, 1947.
Kvasnika et al, *Theirogenology*, vol. 31, pp. 963–971, (May 1989).
Clark et al, *Aust. Vet. J.*, vol. 60, pp. 178–179, 1983.
Clark et al, *Aust. Vet. J.*, vol. 61, pp. 65–66, 1984.
Reece et al, *Aust. Vet. J.*, vol. 57, pp. 352–353, 1981.
Phenotypes and Protein–Epitope Phenotypic Variation among Fresh Isolates of Trichomonas vaginalis, John F. Alderete et al., Infection and Immunity, May 1987, vol. 55, No. 5, pp. 1037–1041.
Specific Parasitism of Purified Vaginal Epithelial Cells by Trichomonas vaginalis, John F. Alderete et al., Infection and Immunity, Oct. 1988, vol. 56, No. 10, pp. 2558–2562.
Infection with Trichomonas Foetus in Heifers, Justin Andrews et al., Oct. 7, 1937, pp. 235–249.
Vaccination Studies on Bovine Trichomoniasis, Banner Bill Morgan, Jan. 1947, pp. 54–56.
Trichomonas Foetus Infection and Bovine Reproduction, David E. Bartlett, pp. 343–347.
Diagnosis, Treatment, and Control of Bovine Trichomoniasis, R. H. BonDurant, Continuing Education Article #10, vol. 7, No. 3, Mar. 1985, S179–S188.
Trichomoniasis in California, Bob BonDurant et al., California Cattleman, Feb. 1988, pp. 10–11.
Tritrichomonas foetus: Preparation of Monoclonal Antibodies with Effector Function, Donald E. Burgess, Experimental Parasitology 62, 266–274 (1986).
The frequency of infertility and abortion in cows infected with Tritrichomonas foetus var. brisbane, B. L. Clark et al., Australian Veterinary Journal, vol. 63, No. 1, Jan. 1986, pp. 31–32.
Infection of Bulls with Tritrichomonas Foetus through Mating with Infected Heifers, B. L. Clark et al., Australian Veterinary Journal, vol. 50, No. 4, Apr. 1974, p. 180.
The effect of Tritrichomonas foetus infection on calving rates in beef cattle, B. L. Clark et al., Australian Veterinary Journal, vol. 60, Mar. 1983, pp. 71–74.
Studies on the Transmission of Tritrichomonas Foetus, B. L. Clark et al., Australian Veterinary Journal, vol. 53, Apr. 1977, pp. 170–172.

(List continued on next page.)

*Primary Examiner*—Jeffrey E. Russel
*Assistant Examiner*—Abdel A. Mohamed
*Attorney, Agent, or Firm*—Darby & Darby

[57] ABSTRACT

This invention provides a bovine vaccine composition comprising an immunogenically active component having inactivated bovine Trichomonas cells or antigens derived therefrom, in combination with an effective amount of an immunogenically suitable adjuvant; and a veterinary pharmaceutically acceptable carrier or diluent. The vaccine composition is useful to prevent Tritrichomonas (Trichomonas), e.g., *T. foetus*, infection in bovine, and may also be combined with other vaccine compositions or therapy. A method for preventing Trichomonas infection in bovine is also provided.

6 Claims, No Drawings

OTHER PUBLICATIONS

Incidence of Tritrichomonas Foetus in Young Replacement Bulls following Introduction into an infected Herd, H. R. Christensen et al., Australian Veterinary Journal, vol. 53, Mar. 1977, pp. 132–134.

Control of Trichomoniasis in a Large Herd of Beef Cattle, B. L. Clark et al., Australian Veterinary Journal, vol. 50, Oct. 1974, pp. 424–426.

Experimental Infection of Bulls with Tritrichomonas Foetus, B. L. Clark et al., Australian Veterinary Journal, vol. 50, May 1974, pp. 189–191.

Identification of a Surface Antigen of Trichomonas vaginalis, Roberta J. Connelly et al., Infection and Immunity, Aug. 1985, vol. 49, No. 2, pp. 270–274.

Observation on the Incidence and distribution of Serotypes of Tritrichomonas Foetus in Beef Cattle in North-Eastern Australia, D. P. Dennett et al., Australian Veterinary Journal, vol. 50, Oct. 1974, pp. 427–431.

Epidemiologic and economic analyses of an unusually long epizootic of trichomoniasis in a large California dairy herd, W. J. Goodger et al., JAVMA, vol. 189, No. 7, Oct. 1, 1986, pp. 772–776.

Characterization of tritrichomonas foetus antigens, using bovine antiserum, Mark R. Hall et al., AM J Vet Res, vol. 47, No. 12, Dec. 1986, pp. 2549–2553.

A Rapid Method for the Detection of Antibodies to Cell Surface Antigens: A Solid Phase Radioimmunoassay Using Cell Membranes, Frank D. Howard et al., Journal of Immunological Methods, 38(1980) 75–84.

Antigenic relationships among field isolates of Tritrichomonas foetus from cattle, Juch-Chin Huang et al., Am J Vet Res., vol. 50, No. 7, Jul. 1989, pp. 1064–1068.

Bovine Trichomoniasis: Diagnosis and Treatment, Paul B. Kimsey et al., JAVMA, vo. 177, No. 7, pp. 616–619.

The Pathogenesis of Tritrichomonas Foetus Infection in the Bull, I. M. Parsonson et al., Australian Veterinary Journal, vol. 50, Oct. 1974, pp. 421–423.

Early Pathogenesis and Pathology of Tritrichomonas Foetus Infection in Virgin Heifers, I. M. Parsonson et al., J. Comp. Path. 1976, vol. 86, pp. 59–66.

Growth and cytopathogenicity of Trichomonas vaginalis in Tissue Cultures, Frank F. Pindak et al., Journal of Clinical Microbiology, Apr. 1986, pp. 672–678.

The Bovine Immune Response to *Tritrichomonas foetus*, Doug Redelman et al., Manuscript dated Oct. 27, 1986, pp. 1–24 and 6 Sheets of Drawings.

Fetal and Placental Lesions in Bovine Abortion Due to Tritrichomonas foetus, J. C. Rhyan et al., Vet. Pathol, 25: 350–355 (1988).

Bovine Trichomoniasis, A. Yule et al., pp. 73–77.

Bovine Trichomoniasis, S. A. Skirrow et al., Veterinary Bulletin 1988, vol. 58, No. 8, Aug. 1988, pp. 591–603.

Nature of Immunity in the Male Bovine Reproductive Tract based upon Responses to *Campylobacter fetus* and *Trichomonas fetus*, A. J. Winter et al., From the Ruminant Immune System edited by John E., Butler (Plenum Publishing Corporation, 1981), pp. 745–752.

BOVINE VACCINE COMPOSITIONS AND METHOD FOR PREVENTING TRICHOMONAS INFECTIONS USING SAME

The present invention provides a bovine vaccine composition and a method for preventing Trichomonas infections in bovine using such vaccine composition. More particularly, this invention relates to a bovine vaccine composition comprising an immunologically active component, i.e., inactivated bovine Trichomonas cells or antigens derived therefrom in combination with an effective amount of an immunogenically stimulating adjuvant, and veterinary pharmaceutically acceptable carriers or diluents therefor.

BACKGROUND OF THE INVENTION

Trichomoniasis is a venerally transmitted disease of cattle which may cause infertility, early and late abortions or uterine infections, further resulting in varying degrees of reproductive inefficiency. The causative agent for trichomoniasis is the parasitical protozoan, Tritrichomonas (Trichomonas) e.g., *T. foetus.*

Trichomoniasis is not a new disease but reported incidence has increased due to improved diagnostic procedures. Movement of cattle from infected areas has also expanded the incidence of the disease. Since there are no viable signs of trichomoniasis, it may go undetected until a producer becomes alarmed by such signs as cows returning to heat at the end of the breeding period, calves of varying ages and sizes at weaning, or a strung-out calving season, and, in response to such signs, the producer takes a critical look at his herd's reproductive efficiency.

The disease is highly transmissible. One infected bull results in herd infection, since a bull infects 80-90% of the cows he services. This can result in calf crop reductions as high as 40% or even more. Losses due to *T. foetus* infection are estimated to be in excess of $500 million annually. One hundred cow herd losses can total $16,000-$20,000.

The *T. foetus* is a protozoan that lives in the crypts (wrinkles or folds) on the mucosal surface of the penis and prepuce of the bull. These organisms are transmitted to the cow only by breeding. If the cow is exposed to *T. foetus* at the time of breeding, these tiny protozoa grow and multiply on the lining of the uterus, causing an inflammation (metritis) which eventually disrupts the placental circulation supplying nutrients to the embryo and results in death of the embryo within the first 30-60 days of pregnancy. Since the embryo is so small, the only outward sign may be a uterine infection with minimal vaginal discharge. Carrier cows do exist, which further complicates *T. foetus* bovine infection in cows. Typically, these chronically infected cows carry a calf to term while infected with the *T. foetus* organism. Clean bulls bred to carrier cows can result in the infection of the entire herd. Culling bulls will do no good so long as carrier cows remain in the herd.

The infection in the bull is completely without symptoms. Although young bulls may become infected, they are relatively resistant due to the lack of crypts on the mucous lining of the penis and prepuce. These folds in the mucous lining provide the necessary environment for the replication of the *T. foetus*. As a bull matures (usually at 2½ to 3 years), these crypts become more pronounced, providing a more suitable environment for the *T. foetus*. While the Trichomonads grow in these crypts, they do not stimulate the bull's immune system, thus the bull remains infected.

Past attempts to immunize or vaccinate cattle against Trichomonas infection have not been very successful for a variety of reasons, including any or all of the following: 1) vaccines developed for infected bulls failed to clear or prevent infection in older bulls; 2) vaccines developed for cows failed to prevent infection in bulls; 3) vaccines developed for cows failed to stimulate local immunity in the cervico-vaginal cavity.

It is an object of the present invention to provide an effective bovine vaccine composition having high antigen load and including a very potent adjuvant which will stimulate localized mucosal immunity against *Trichomonas foetus* when administered systemicly to a subject bovine.

It is another object of the present invention to reduce the incidence of abortion among cows susceptible to Trichomonas infection.

It is still yet another object of this invention to increase reproductive or breeding efficiency among bovine animals (bulls and cows) susceptible to Trichomonas infection.

Yet another object of the present invention is to provide a method for preventing Trichomonas infection in cattle by immunizing these animals with an efficacious vaccine composition.

These and other objects will become more apparent in light of the detailed description which follows.

SUMMARY OF THE INVENTION

The present inventors have unexpectedly discovered that an immunogenically active component can be made and usefully incorporated into a vaccine composition for preventing Trichomonas infections in bovine, i.e., cattle, cows, bulls, heifers. The immunogenically active component has inactivated, e.g., chemically inactivated, bovine Tritrichomonas (Trichomonas) cells or antigens derived therefrom, such as outer membrane extracted antigen. The immunogenically active component is combined with an effective amount of an immunogenically stimulating adjuvant, and a veterinary pharmaceutically acceptable carrier or diluent therefor.

DETAILED DESCRIPTION OF THE INVENTION

All literature references, patents and patent applications cited in this specification are hereby incorporated by reference in their entirety.

The present invention provides a vaccine composition comprising an immunogenically active component having inactivated bovine Trichomonas cells, e.g. *T. foetus* or antigens derived therefrom in combination with an effective amount of an immunogenically stimulating adjuvant; and a veterinary pharmaceutically acceptable carrier or diluent therefor.

As used herein, the term "immunogenically active" component refers to the ability of the component described herein to stimulate an immune response, i.e., to cause the production of antibodies and/or cell-mediated response when introduced into a subject (mammal, e.g., bovine). More specifically, the term "immunogenically active" component refers to the ability of this component to stimulate secretory antibody and/or cell-mediated response production in local mucosal regions, e.g., cervico-vaginal cavity, when administered systemically as a vaccine composition according to the present invention.

The Trichomonas cells, e.g., *T. foetus* cells, or antigens derived therefrom which are used to make the immunogenically active component of the vaccine composition can be isolated from the fluids or tissues of mammalian, e.g., bovine (bulls, cows), sources or specimens obtained from animals infected with the Trichomonas protozoan. Such sources or specimens include, for example, vaginal, cervical, uterine, prepuce, scrapings and secretions. In particular, the Trichomonas protozoans can be isolated from the vaginal, cervical and uterine fluids from infected cows which have aborted calves, and also from the preputial sheath from infected bulls. The Trichomonas protozoans can be maintained in the infected bovine, or in suitable nutrient media known in the art, such as, for example, Diamond's modified medium which is prepared by the method described by Diamond, L. S., (1983) Human dwelling protozoa: Entamoeba, Trichomonads and Grandes. In *In Vitro Cultivation of Protozoan Parasites*, edited by J. B. Jensen, CRC, Boca Raton, pp. 65-109 (not more than 10% serum protein is added to the Diamond medium).

Diamond's medium contains the following composition:

|  | Gm/Liter |
|---|---|
| Casein Hydrolysate | 20.0–50.0* |
| Yeast Extract | 10.0–50.0* |
| Maltose | 5.0 |
| L-Cysteine Hydrochloride | 1.0 |
| L-Ascorbic Acid | 0.2 |
| Dibasic Potassium Phosphate (anhydrous) | 0.8 |
| Monobasic Potassium Phosphate (anhydrous) | 0.8 |

*Batch to batch variation influences growth of the organism. Concentration levels vary according to the batch of new material and growth obtained with the organism.

The powdered media is dissolved in deionized water and the media is then sterilized by autoclaving at 121° C. The media is labeled and may be stored at room temperature until use. To the prepared Diamond's medium, as noted above, not more than 10% serum protein is added.

The Trichomonas protozoans can be isolated from the fluids or tissues as described above, e.g., vaginal fluid, or preputial washings of infected bovine animals and cultured in suitable nutrient media. The Trichomonas protozoans can be separated from the culture media using techniques well-known in the art, such as centrifugation, filtration and the like.

Following their separation as whole cell isolates, the Trichomonas protozoans can be inactivated by conventional inactivation means known in the art. For example, chemical inactivation of the Trichomonas whole cell isolates can be carried out by contacting the cells with a chemical inactivating agent. Such agents include by way of non-limiting example, binary ethylenimine, beta-propriolactone, formalin, merthiolate, glutaraldehyde, sodium dodecyl sulfate, Triton-100, or a combination of any of these agents in an aqueous suspension. Preferred as a chemical inactivating agent is merthiolate at a final concentration of 1:10,000 for 24 to 72 hours.

The Trichomonas cellular isolates can also be inactivated by heat or psoralen in the presence of ultraviolet (UV) light.

After inactivation, the inactivated Trichomonas whole cells can be adjusted to an appropriate concentration of from about $10^8$ to about $10^9$ in combination with an immunogenically stimulating adjuvant. When antigens derived from Tritrichomons (Trichomonas) cells, e.g., *T. foetus* cells, are employed, a suitable amount of protein or antigen per dose may be used, for example, 50 to 100 ug/dose.

As used herein the term "immunogenically stimulating adjuvant" refers to an agent, compound or the like, which potentiates or stimulates the immune response in a subject animal when administered in combination with the inactivated whole cells. Thus, the immune response, elicited by the inactivated whole cell-adjuvant combination, as measured by antibody and/or cell-mediated response, will generally be greater than that provoked by the inactivated whole cells alone.

The immunogenically stimulating adjuvants augment the immune response provoked by the inactivated Trichomonas cells. The inactivated Trichomonas cells may or may not elicit a desired immune response, e.g., a local mucosal, e.g., vaginal, immunity, when systemically administered alone. An essential feature of the present invention is the combination of the inactivated Trichomonas cells and immunogenically stimulating adjuvant, which provide the desired immune response.

Non-limiting examples of the immunogenically stimulating adjuvants used in the practice of the present invention are surfactants, e.g., hexadecylamine, octadecylamine, lysolecithin, dimethyldioctadecyl-ammonium bromide, N,N-dioctadecyl-N'-N-bis(2-hydroxyethylpropane diamine), methoxyhexa-decyl-glycerol and pluronic polyols, saponin, Quil A; polyanions, e.g., pyran, dextran sulfate, poly IC (polynucleotide complex of polyinosinic-polycytidylic acid) polyacrylic acid, carbopol, aluminum hydroxide, aluminum phosphate; peptides, e.g., muramyl dipeptide, dimethylglycine, tuftsin; oil emulsions, immunomodulators, e.g., interleukin-1, interleukin-2; or combinations of any of the foregoing adjuvant agents. Preferred as an immunogenically stimulating adjuvant is an adjuvant containing, for example, 1–20% by volume of an oil-in-water emulsion and 0.1–10 ug chlorotoxin or 0.5 to 10 mg saponin per dose, whether such dose is 2- or 5- or 10 ml/dose.

It has been discovered that the adjuvants described above will act in effective amounts to immunogenically stimulate the inactivated Trichomonas cells or antigens derived therefrom when combined therewith, to form the active component of the vaccine composition of this invention. As used herein, the effective amount of the immunogenically stimulating adjuvant can comprise from about 1% to about 50%, preferably from about 5% to about 20%.

The vaccine composition of the present invention further comprises a veterinary pharmaceutically acceptable carrier or diluent. Such a carrier or diluent useful in the practice of the present invention is saline. Preferred is saline, e.g., 2.0 mL saline.

As further embodiments of the present invention, the vaccine composition can be administered, for example, by incorporating the active component into liposomes. Liposome technology is well-known in the art having been described by Allison, A. C. and Gregoriades, G., Liposomes as immunologic adjuvants. *Nature* 252:252-54 (1974); and Dancy, G. F., Yasuda, T., and Kinsky, S. C., Effect of liposomal model membrane composition on immunogenicity. *J. Immunol.* 120:1109-13 (1978). In addition, the active component can be conjugated to suitable biological compounds or materials, such as, for example, polysaccharides, peptides, proteins, or a combination of any of the foregoing. Conjugated vaccines are described by Coon, J., and Hunter, R. L., Selective stimulation of delayed hyperinsitivity by a lipid conjugated protein antigen. *J. Immunol.* 110:183-90 (1973).

It is advantageous to formulate the vaccine composition of this invention in dosage unit form to facilitate administration and insure uniformity of dosage. Thus, in another embodiment, this vaccine composition can be formulated in dosage unit form comprising at least about $1 \times 10^6$ inactivated Trichomonas cells, preferably at least about $5.0 \times 10^7$ cells.

In a further embodiment, the vaccine composition can comprise a parenteral injectable form, again to ease its administration to a subject bovine.

The present invention provides a method for preventing Trichomonas infection in bovine comprising administering to a bovine in need of such prevention an effective amount of the vaccine composition described above.

The routes of administration contemplated by the present invention are parenteral, e.g., subcutaneous, intramuscular, intraperitoneal and intradermal. Preferred routes of administration are subcutaneous and intramuscular.

It has been discovered that the vaccine composition of the present invention is useful to prevent Trichomonas infection in bovine that need such protection when administered parenterally, e.g., subcutaneously or intramuscularly, in effective amounts and according to a schedule dictated by the breeding of the bovine. For example, the vaccine composition has been found to be effective in preventing Trichomonas infection when the final dose is administered at least about fourteen (14) days before breeding of the treated animal. In this way, the treated animal has time to build immunity prior to breeding. An effective regimen of treatment includes administering the vaccine composition, for example, in dosage unit form as described above, at least about two times, with each administration separated by about two (2) to about four (4) weeks, i.e., from about fourteen (14) to about thirty (30) days or so.

A preferred treatment schedule would include parenteral administration, e.g., subcutaneous or intramuscular injection, at least about 4-6 weeks prior to breeding. Because at least two administrations (injections) are preferred, these administrations (injections) could be given, for example, at about six (6) weeks and about two (2) weeks, respectively, before breeding of the treated animal.

This invention provides a multi-vaccine composition comprising the vaccine composition as described above, and at least one vaccine composition directed against a pathogen selected from the group consisting of *Leptospira canicola, L. icterohaemorrhagiae, L. pomona, L. hardjo, L. grippotyphosa* and *Campylobacter fetus*, or a combination or any of the foregoing.

The working examples set forth below are intended to illustrate the invention without limiting its scope.

EXAMPLE 1

Vaccine Preparation

A bovine vaginal isolate of *T. foetus* was obtained from the vaginal fluids of a cow which had been naturally infected with *Trichomonas foetus* and which had recently aborted a calf. The isolate was cultivated in a modified Diamond's medium at 37° C. in air to a density of $1 \times 10^7$ protozoans/mL. The modified medium was prepared from the following composition:

|  | Gm/Liter |
| --- | --- |
| Casein Hydrolysate | 20.0-50.0 |
| Yeast Extract | 10.0-50.0 |
| Maltose | 5.0 |
| L-Cysteine Hydrochloride | 1.0 |
| L-Ascorbic Acid | 0.2 |
| Dibasic Potassium Phosphate (anhydrous) | 0.8 |
| Monobasic Potassium Phosphate (anhydrous) | 0.8 |

The powdered media was dissolved in deionized water and the media was then sterilized by autoclaving at 121° C. To the prepared Diamond's medium not more than 10% serum protein was added.

*Trichomonas foetus* protozoans were harvested by centrifugation, resuspended in a small volume of saline adjusted to pH 7.2. Merthiolate was added to this solution to a final concentration of 0.0001% and incubated at 4° C. for 24 hours.

The vaccine was formulated by suspending the appropriate volume of inactivated cells in an adjuvant containing 1-20% by volume of an oil-in-water emulsion and 0.5 to 10 mg saponin per 2 mL dose.

EXAMPLE 2

Challenge and Isolation of *T. foetus*

Fourteen to 35 days after vaccination i.e., following second vaccination, challenge was initiated. 120 heifers were challenged by breeding with persistently infected bulls and/or intra-vaginal infusion by $1 \times 10^8$ protozoans by an infectious isolate of *T. foetus* which had not been subcultured more than four times. Mucous from the reproductive tract of each heifer was sampled thirty (30) days post breeding and weekly thereafter *T. foetus* was isolated at 37° C. in screw capped tubes (15×20 mm) containing 10.0 mL of modified Diamond's medium (prepared to according to Example 1) without agar. Cultures were held 12-14 days before isolation attempts were determined negative.

EXAMPLE 3

Antibody Response to Subcutaneous Injection of Vaccine 60 heifers were injected subcutaneously with a vaccine prepared according to Example 1. The heifers received two injections of vaccine ($5 \times 10^7$ whole cells in 2.0 mL saline containing 1-20% oil-in-water emulsion and 0.5-10 mg of saponin at 14 day and 21 day intervals. The antibody levels were determined by indirect immunofluorescent antibody (IFA) assay conducted as follows: Slides were prepared using *T. foetus* organisms washed two to three times in PBS and resuspended in PBS. Slides were air dried before fixing in chilled acetone. Slides were then flooded for 30 minutes at 37° C. with two-fold dilutions of test sera before rinsing in PBS. A dilution of FITC conjugated anti IgG sera was then added to each slide. The slides were incubated at 37° C. for 30 minutes, washed in PBS, mounted and read microscopically using a fluorescent microscope. The antibody levels were also determined by a culture protection i.e., serum neutralization (SN) assay conducted as follows: Two-fold dilutions of test sera were incubated with a quantitated amount of viable *T. foetus*. Neutralization was determined by cultivating the serum-organism mixtures in confluent MDBK monolayers. Viable *T. foetus* will cause a characteristic cytopathic effect to the monolayer and neutralized *T. foetus* will cause no cytopathic effect. The results of these assays are summarized in Table 1 below.

TABLE 1*

| Time (Days Following Vaccinations ($V_1$-$V_2$) | Protection | | | | | |
|---|---|---|---|---|---|---|
| | Vaccinates | | Controls | | Freunds | |
| | IFA | SN | IFA | SN | IFA | SN |
| $V_1$ (0 days) | 5 | 34 | _5 | 32 | _5 | 32 |
| $V_2$ (28 days) | 746 | 104 | _5 | 32 | 264 | 74 |
| 28 day post $V_2$ | 1715 | 588 | _5 | 32 | 528 | 446 |
| 75 days post challenge | 264 | 52 | _5 | 32 | 606 | 74 |

*Trichomonas appears sensitive to non-immune bactericidal factors in serum diluted 1:32 or less.

The data summarized in Table 1 indicates that all the heifers, that were vaccinated according to the present invention, developed humoral IFA and SN antibody titers following the first vaccination and an anamnestic response following the second vaccination.

The significance in protection of humoral antibody stimulation has been questioned by some investigators. It has been demonstrated by at least one study that vaginal/uterine infection by a pathogen does not stimulate serum antibody. (S. Skirrow, R. Bon Durant, Abstract #214, Conference of Research Workers in Animal Disease, 1988, p. 38) Systemic immunization can stimulate significant local antibody in the vagina. Significant correlation has been demonstrated with the cell-mediated immune (CMI) response. In any event, as shown by the results in Table 1, the immune response elicited by the immunogenicity serial performed in accordance with this invention was more effective than Freund's antibody titer following primary vaccination, as well as an anamnestic response. Therefore, the duration and intensity of local immunity conferred has been found to increase by using multiple vaccinations. A vaccine comprising inactivated *T. foetus* has also been found effective to actively immunize susceptible cattle against trichomoniasis.

Trichomonas was recovered from 9 to 10 non-vaccinated controls; recovery rate from two heifers was 12 weeks, from one heifer each for 11 weeks, 10 weeks, 8 weeks, 5 weeks and 3 weeks, respectively. Trichomonas was also recovered from two heifers for one week. A total of 84 samples were taken from the control group through the end of Month 3 and 104 samples through the end of detectable infection as designated by five consecutive negative cultures.

The results of the recovery procedure, as evidence of the efficacy of the vaccine composition of the present invention, are illustrated in Table 2 below.

TABLE 2

Trichomonas Recovery from Vaccinated and Non-Vaccinated Calves Following Exposure to Infected Bulls and Artificial Infusion

| Calf No. | Month 1 | | Month 2 | | | | Month | | | | | Month 4 | | | |
|---|---|---|---|---|---|---|---|---|---|---|---|---|---|---|---|
| | 22 | 28* | 06* | 13 | 20* | 27 | 08 | 10 | 17 | 24 | 31 | 07 | 14 | 25 | 18 |
| Vaccinates | | | | | | | | | | | | | | | |
| 9 | — | — | — | — | — | — | — | — | — | — | | | | | |
| 13 | — | — | — | — | — | — | — | — | — | | | | | | |
| 17 | | | — | + | + | — | — | — | — | — | — | | | | |
| 37 | | | — | — | — | — | — | — | — | — | | | | | |
| 42 | | | — | — | — | — | — | — | — | — | | | | | |
| 57 | | | — | + | + | — | — | — | — | — | | | | | |
| 61 | | | — | — | — | — | — | — | — | — | | | | | |
| 63 | | | — | — | — | — | — | — | — | — | | | | | |
| 92 | | | — | — | + | — | — | — | — | — | | | | | |
| 111 | | | — | — | — | — | — | — | — | — | | | | | |

Total samples through end of Month 3 = 87% = 5.7%, i.e., 5.7% of all samples from vaccinated heifers were positive for Trichomonas infection.

| Control | | | | | | | | | | | | | | | |
|---|---|---|---|---|---|---|---|---|---|---|---|---|---|---|---|
| 18 | | | — | + | — | — | — | — | | | | | | | |
| 29 | — | — | — | — | — | + | — | — | — | — | | | | | |
| 40 | | | + | — | + | + | — | — | — | — | — | — | — | — | |
| 51 | | | — | — | — | — | — | — | — | — | — | | | died Month 4, Day 26 | |
| 52 | | | + | + | — | + | + | + | + | + | + | + | + | + | + |
| 56 | | | + | + | — | + | + | + | + | + | + | + | + | + | + |
| 59 | | | + | + | + | + | + | + | + | + | + | + | + | + | + |
| 83 | | | — | — | — | + | — | + | — | — | + | + | + | | |
| 89 | | | + | — | + | + | + | + | + | + | + | + | + | | |
| 95 | | | + | — | — | + | + | + | + | + | + | + | — | — | |

Artificial Infusion:
Month 1, Day 29;
Month 2, Day 6; and
Month 2, Day 20.
Total samples through end of Month 3 = 84% = 51.2%, i.e., 51.2% of all samples from non-vaccinated controls were positive.
Total samples through Month 4, Day 25 = 104% = 60.6%, i.e., 60.6% of all samples taken from controls through month 4 were positive.

Statistical Analysis: t-Test; = 18, t = 3.72, p = 0.001.

As shown by the results in Table 2, the percent positive cultures were 51.1 and 60.6, respectively. The average number of days of positive isolation was 44.1 days. These results indicate that 1) 70% of the controls exhibited an infection characterized by positive isolation on three sampling days as compared to none, i.e., 0%, of the vaccinates; 2) there was a 95.2% reduction in the number of positive samples. Therefore, following infusion, the heifers were successfully exposed to Trichomonas and colonization did occur in the controls. Recovery of Trichomonas from the vaccinates was significantly reduced from the challenge control heifers (p=0.001).

The results in Table 2 also indicate that it is more difficult to initially establish an infection in the vaccinates compared to the controls after each cycle in infusion in the heifers; two consecutive weeks from two heifers and one week from one heifer. It is significant that 100% of the vaccinates failed to demonstrate a chronic infective state. A total of 87 samples were taken from the vaccinated group through the end of Month 3 and only 5.7% of these samples were positive. The average number of days of positive isolation was 2.1.

From the results obtained in Example 3 above, particularly Table 2, it can be concluded that vaccination according to the present invention, decreases the ability of the infectious challenge Trichomonas organism to colonize the bovine reproductive tract. It may also be concluded that vaccination according to the present invention increases the clearance of the infectious Trichomonas organism from the bovine reproductive tract.

EXAMPLE 4

Protection Against *T. foetus* Induced Abortion

Thirty-four 18 month old holstein heifers were assigned to control (12), soluble vaccine (11) and whole vaccine (11) groups to determine the effect of Trichomonas foetus vaccines on the reproductive performance of *T. foetus* infected animals. Heifers were bred to *T. foetus* infected bulls beginning two weeks after the second *T. foetus* vaccination. All immunized animals developed antibody titers of at least 1:1,000 following vaccination. In addition, all control and immunized animals became infected with *T. foetus*. However, the duration of infection was approximately two weeks shorter in immunized animals. Approximately 42% (5 of 12) of the control heifers remained *T. foetus* infected for the duration of the experiment, while only 18% (2 of 11) of each of the vaccine groups remained infected for the duration of the experiment. Finally, 27% (3 of 11) of the heifers in each of the vaccine groups were pregnant at slaughter, while none of the control heifers were pregnant at slaughter.

The efficacy of the *T. foetus*-based vaccines of the present invention can be increased by employing immunogenic fractions derived therefrom by methods which are well known in the art. For example, soluble Trichomonas outer envelope antigens which surround the protoplasmic cylinder of protozoans can be readily extracted as disclosed by Kvasnicka, W. G., Taylor, R.E.L., Hands, D., Huang, J.-C. and M. R. Hall, "An Assessment of the Efficacy of Immunization of Cattle with Vaccines Containing *Trichomonas foetus*, 9th Annual Food-Animal Disease Research Conference (1988), Pullman, W. A., which serve to increase immunogenicity.

This fraction may provide immunogens which impart an equal or greater resistance to Trichomonas infection when employed as the active component of a bovine vaccine composition in accordance with the present invention.

This invention has been described with reference to various specific and preferred embodiments and techniques. It should be understood, however, that many variations and modifications can be made by those of ordinary skill in the art while remaining within the spirit and scope of the invention.

What is claimed is:

1. A method of preventing Trichomonas infection in a cow or heifer comprising administering to said cow or heifer an effective amount of the vaccine composition comprising an immunogenically active component having from $1 \times 10^6$ to $1 \times 10^9$ of inactivated bovine Trichomonas cells or antigens derived therefrom per dose in combination with an effective amount of an immunogenically stimulating adjuvant; and a veterinary pharmaceutically acceptable carrier or diluent therefor.

2. The method according to claim 1, wherein said vaccine composition is parenterally administered.

3. The method according to claim 2, wherein said parenteral administration is carried out subcutaneously.

4. The method according to claim 2, wherein said parenteral administration is carried out intramuscularly.

5. The method according to claim 1, wherein said vaccine composition is administered at least fourteen days before breeding of said cow or heifer.

6. The method according to claim 5, wherein said vaccine composition is administered at least two times, each administration separated by 14 to 30 days.

* * * * *